United States Patent [19]

Jha et al.

[11] Patent Number: 5,401,843
[45] Date of Patent: Mar. 28, 1995

[54] PROCESS FOR THE PREPARATION OF CAPROLACTAM

[75] Inventors: Brajesh K. Jha; Ajay S. Chhatre; Bhaskar D. Kulkarni; Subramanian Sivasanker, all of Maharashtra, India

[73] Assignee: Council of Scientific and Industrial Research, New Delhi, India

[21] Appl. No.: 221,180

[22] Filed: Mar. 31, 1994

[51] Int. Cl.$^6$ .......................................... C07D 201/04
[52] U.S. Cl. .................................................. 540/535
[58] Field of Search ........................................ 540/535

[56] References Cited

U.S. PATENT DOCUMENTS 4,359,421 11/1962 Bell et al. ............................ 540/535

Primary Examiner—Robert T. Bond
Attorney, Agent, or Firm—Ladas & Parry

[57] ABSTRACT

A process for the preparation of caprolactam by reacting cyclohexanone oxime with an anionic surfactant and a cosurfactant in dilute sulfuric acid at a temperature in the range of 15° C. to 40° C., neutralising excess acid present in the solution and from the solution by filtration.

10 Claims, No Drawings

PROCESS FOR THE PREPARATION OF CAPROLACTAM

This invention relates to a process for the preparation of caprolactam using micellar solutions, macroemulsions or microemulsion systems. Macroemulsion, Microemulsion and Micellar solutions are pseudo-homogeneous solutions of either oil in water or water in oil, stabilized with the help of a surface active agent and a co-surfactant.

Caprolactam is used as a bulk starting material in the manufacture of nylon-6 polyamide. Caprolactam is also used for the preparation of L-Lysine which is an essential ingredient in animal food.

Prior Knowledge

One of the conventional methods of preparation of caprolactam involves treating cyclohexanone oxime with concentrated sulfuric acid or phosphoric acid, followed by neutralization with liquid ammonia. The reaction is usually carried out at higher temperatures ranging from 50°–150° C. with a control over the temperature. This process makes use of concentrated acids which may be hazardous. Also, this process ends up in formation of equally large quantities of ammonium salts such as ammonium sulfate and ammonium phosphate respectively as unwanted by-product. The purification process of caprolactam usually employs thin film recrification in conjunction with chemical treatments. Double extraction of caprolactam using organic solvent and water is also employed in some cases (For details the following publications may be referred to: i) J. H. Bonfield and J. Northcott in "*Encyclopedia of Industrial Chemical Analysis*", Foster Dee Snell and Leslie S. Ettre (Eds.), Vol. 8, John Willey & Sons Inc., New York, 1969 ii) J. E. Kent and S. Riegel in "*Handbook of Industrial Chemistry*", 8th Ed. p.402, Van Nostrand, New York, 1983). Other commercial process is based on the multistage high pressure reaction of caprolactone and ammonia at elevated temperatures such as 200° C. in the first stage and 365° C. in the second stage. The residence time in the reactors ranges from 1 hour to 5 hours. In many cases, control of the concentration of ammonia and water is very critical since these factors determine the amounts of unwanted by-products such as δ-methylδ-valerolactam. Operation under very high amounts of ammonia or low amounts of water results in formation of so large quantities of reaction intermediates that it becomes very difficult to recycle these even though they are convertible to caprolactam. In another method, Hexahydrobenzoic acid is reacted with nitrosyl sulfuric acid in oleum to produce caprolactam. This method uses nitrosyl sulfuric acid in oleum which may be extremely hazardous. Using nitrosyl sulfuric acid may lead to certain operational problems like corrosion and environmental problems like waste water pollution. Also, this process yields appreciable amount of ammonium sulfate as an unwanted by-product (For details of the last two processes the following publication may be refered to: "*Combine Hydrocarbons and Nitrogen for Profit*", Chemical Process Review No. 8, M. Sitting (Ed.), Noyes Development Corp., Park Ridge, N.J., 1967).

The main objective of the present invention is to provide a process for the preparation of caprolactam where the process will minimize the formation of by products by carrying out the reaction in presence of surface active agents (surfactants) and co-surfactants under mild acid conditions.

One of the strategies is to use an anionic surfactant in the form of either a micellar solution, macroemulsion or a microemulsion in dilute sulfuric acid and to carry out the Beckmann rearrangement of cyclohexanone oxime under this condition. Cationic surfactant or Nonionic surfactants can also be used for this reaction. Since this method makes use of dilute sulfuric acid a relatively small quantity of alkali is needed to neutralize the excess acid Thus largely avoiding the formation of by-product such as ammonium sulfate. The only major by-product formed is cyclohexanone which is reconvertible to cyclohexanone oxime and can be easily recycled as also the surface active agent which separates during the neutralization. Also, since the reaction is carried out at ambient conditions of temperature and pressure the energy requirements are not significant. Besides the formation of caprolactam, the present method also yields minor amounts of other side products such as amino caproic acid and its dimer which are also useful in the production of nylon-6 polyamide.

A micellar solution is a solution of a surfactant in an aqueous or organic solvents like benzene, tolune, xylene, hexane, heptane, octane and the like. These solutions are of two kinds, namely oil-in-water or water-in-oil types. A macroemulsion is a coarse and unstable emulsion of oil-in-water or water-in-oil. A microemulsion is a special case of a micellar solution and is an extremely stable oil-in-water or a water-in-oil emulsion. The present invention exploits one very important property of micellar, macroemulsion and microemulsion solutions for carrying out this reaction. The particular property of interest concerns the anomalous hydrogen ion concentration experienced in vicinity of the macroemulsion microemulsion or micellar solution globules. Since the Beckmann rearrangement reaction is a $H^+$-ion catalysed reaction the catalysis of this reactions, at least impart, depends on the ability of micelles to concentrate the reagents into the small volume of the Stern layer where the effective $H^+$ ionic strength is maximum relative to the bulk ionic strength. The reaction rate constant of the catalyzed reactions generally depends on the extent of the sulfactant concentration and generally exhibit maxima. Such a maxima occurs due to two opposing effects. The higher concentration of surfactants extracts more reagents into the micelles. It also leads to increasing total volume of the Stern layer thereby diluting the concentration at the micellar surface. In general it is anticipated that all those reactions which involve the participation of hydrogen ions either as a reactant or as a catalytic species can benefit substantially in such media. For further details of the related mechanism, the following publications may be referred to:

1. O. A. Amire, *J Colloid Int. Sci.* 126(2), 508(1988).
2. C. A. Bunton and B. Wolfe, *J. Am. Chem. Soc.* 95(11), 3742(1973).
3. C. A. Bunton; G. Savelli, *Adv. Phys. Org. Chem.* 22,213(1986).

The rearrangement of cyclohexanone oxime to caprolactam, requires the participation of hydrogen ions as a catalytic species. In the present invention this has been achieved by using a surfactant in the form of a micellar solution, macroemulsion or microemulsion solution in dilute sulfuric acid.

Accordingly, the present invention provides an process for the preparation of caprolactam using a surfactant.

Thus, the present invention provides a process for the preparation of caprolactam which comprises preparing a aqueous solution of the anionic surfactant in dilute sulfuric acid, adding to this solution cyclohexanone oxime under constant stirring, adding a co-surfactant, if required, to the mixture, maintaining the solution at a temperature in the range of 15° C. to 40° C. for a period ranging from 10 minutes to 3 hours, neutralizing the excess acid with an aqueous solution of alkali filtering, extracting the filtrate with the solvent, and recycling the residue containing the unreacted cyclohexanone oxime and the surfactant.

The surfactant is used in the form of a micellar solution, a macroemulsion solution, or a microemulsion solution in dilute sulfuric acid wherein the concentration of the surfactant may be in the range of 20 gm/lit to 80 gm/lit (lit=liter), preferably 80 gm/lit, and that of the sulfuric acid in the range of 0.1 moles/lit to 2.5 moles/lit preferably 1.5 moles/lit, adding to this solution cyclohexanone oxime in the range from 10 gm/lit to 100 gm/lit. Preferably 50 gm/lit under constant stirring, adding a co-surfactant, if required, to the mixture in the of 2 ml/lit to 50 ml/lit, maintaining the solution at a temperature in the range of 15° C. to 40° C. for a period ranging from 10 minutes to 3 hours, neutralizing the excess acid with aqueous solution of an alkali, filtering, extracting the filtrate with the solvent, and recycling the residue containing the unreacted cyclohexanone oxime and the surfactant. Examples of surfactant are sodium dodecyl sulfate sodium dodecyl benzene sulfonate, sodium salt of dioctyl sulfosuccinate and the like. Examples of co-surfactant are propyl alcohol, i-pentanol, n-pentanol, n-pentyl amine, i-propyl amine and alike. The invention provides conversion of cyclohexanone oxime in the range of 80 to 90% and yield of caprolactam in the range of 68 to 90%, with formation of cyclohexanone which can be easily recovered and recycled.

The invention is illustrated by the examples given below, which should however not be construed to limit the scope of the present invention.

EXAMPLE 1

Take 9.2 gm of aqueous solution of 1.08N sulfuric acid in a small round bottom flask. Dissolve in this solution 0.8 grams of sodium dodecylsulfate (SDS) by mild stirring. Keep the flask in a water bath maintained at temperature of 30° C. A micellar solution of SDS is formed. To this micellar solution, add 0.5 gm of cyclohexanone oxime and stir the mixture mildly for 1 hour. Remove the flask from the water bath and neutralize the solution using aqueous solution of sodium hydroxide. Filter the solution using Whatman No. 1 filter paper. Measure the amount of filtrate and the residue and extract the filtrate with 5 ml of benzene in two steps of 2.5 ml each. Analyze the benzene layer, the aqueous layer and the residue obtained as above by Gas Chromatography for the amount of cyclohexanone oxime, cyclohexanone and caprolactam.

EXAMPLE 2

Take 9.2 gm of aqueous solution of 2.16N sulfuric acid in a small round bottom flask. Dissolve in this solution 0.8 grams of sodium dodecylsulfate (SDS) by mild stirring. Keep the flask in a water bath maintained at temperature of 30° C. A micellar solution of SDS is formed. To this micellar solution, add 0.5 gm of cyclohexanone oxime and stir the mixture mildly for 1 hour. Remove the flask from the water bath and neutralize the solution using aqueous solution of sodium hydroxide. Filter the solution using Whatman No. 1 filter paper. Measure the amount of filtrate and the residue and extract the filtrate with 5 ml of toluene in two steps of 2.5 ml each. Analyze the toluene layer, the aqueous layer and the residue obtained as above by Gas Chromatography for the amount of cyclohexanone oxime, cyclohexanone and caprolactam.

EXAMPLE 3

Take 200 ml of aqueous solution of 3.0N sulfuric acid in a round bottom flask. Dissolve in this solution 16 grams of sodium dodecyl sulfate (SDS) and 5.3 gm 1-pentanol by mild stirring. A microemulsion is thus formed. Keep the flask in a water bath maintained at temperature of 25° C. To this microemulsion, add 10.0 gm of cyclohexanone oxime and stir the mixture mildly for 2 hours. Remove the flask from the water bath and neutralize the solution using aqueous solution of ammonia. Filter the solution using Whatman No. 1 filter paper. Measure the amount of filtrate and the residue and extract the filtrate with 100 ml of benzene in steps of 50, 25, and 25 ml respectively. Analyze the benzene layer, the aqueous layer and the residue obtained as above by Gas Chromatography for the amount of cyclohexanone oxime, cyclohexanone and caprolactam.

EXAMPLE 4

Take 200 ml of aqueous solution of 2.98N sulfuric acid in a round bottom flask. Dissolve in this solution 14 grams of sodium dodecyl sulfate (SDS) by mild stirring. Keep the flask in a water bath maintained at temperature of 40° C. A micellar solution of SDS is formed. To this micellar solution, add 10.0 gm of cyclohexanone oxime and stir the mixture mildly for 2 hours. Remove the flask from the water bath and neutralize the solution using aqueous solution of sodium hydroxide. Filter the solution using Whatman No. 1 filter paper. Measure the amount of filtrate and the residue and extract the filtrate with 100 ml of benzene in steps of 50, 25, and 25 ml respectively. Analyze the benzene layer, the aqueous layer and the residue obtained as above by Gas Chromatography for the amount of cyclohexanone oxime, cyclohexanone and caprolactam.

EXAMPLE 5

Take 200 ml of aqueous solution of 2.16N sulfuric acid in a round bottom flask. Dissolve in this solution 6.8 gm of sodium dodecyl benzene sulfonate (SDBS) and 1.3 gm of benzene by mild stirring. Keep the flask in a water bath maintained at temperature of 40° C. A macroemulsions of benzene in sulfuric acid is formed. To this macroemulsion, add 14.0 gm of cyclohexanone oxime and stir for 2½ hours. Neutralize the excess acid using Whatman No. 1 filter paper to remove or recycle the the unreacted cyclohexanone oxime. Separate the organic and aqueous layers of the filtrate. Wash the aqueous layer with 3×10 ml benzene and add the benzene washing with the main organic layer. Analyze the benzene layer, the aqueous layer and the unreacted cyclohexanone oxime as obtained above by Gas Chromatography for the amount of cyclohexanone oxime, cyclohexanone and caprolactam.

EXAMPLE 6

Take 200 ml of aqueous solution of 2.16N sulfuric acid in a round bottom flask. Dissolve in this solution 3.22 gm of sodium dodecyl benzene sulfonate (SDBS) and 3.22 gm of isopropyl alcohol and 6.93 gm of benzene. This forms a microemulsion of benzene in sulfuric acid, add 11.3 gm of cyclohexanone oxime and stir for 10 minutes. Neutralize the excess acid by liquid ammonia. Add 0.6 gm sodium chloride and 0.1 gm potassium carbonate to deemulsify the microemulsion. Filter the solution using Whatman No. 1 filter paper. Remove or recycle the residue. Separate the filtrate in a separating funnel. Wash the aqueous layer with 3×10 ml benzene and add the benzene washing to the main organic layer. Analyze the benzene layer, the aqueous layer and the residue by chemical methods or Gas Chromatography for the amount of cyclohexanone oxime, cyclohexanone, caprolactam and SDBS.

The main advantages of the process are,

1. The process makes use of dilute sulfuric acid thereby circumventing the usage of large amounts of alkali for neutralization.
2. The process is carried out under ambient conditions of temperature and pressure, thereby reducing largely the power requirements.
3. Micellar or microemulsion solutions provide large interfacial areas and thus help in enhancing the reaction rate.
4. The surfactant can be easily recovered and hence recycled.
5. Cyclohexanone formed can be easily recovered, converted to cyclohexanone oxime, and subsequently recycled.
6. The process can be converted into a continuous process, thus reducing the overall time required as compared to batch process.
7. The process offers conversion in the range of 80 to 90%, yield of caprolactam in the range of 68 to 90%, and that of cyclohexanone in the range of 14 to 30%. The cyclohexanone formed can be recycled.

We claim:

1. A process for the preparation of caprolactam which comprises preparing a micellar solution, or a macroemulsion, or a microemulsion of an anionic surfactant in dilute sulfuric acid, adding to this solution cyclohexanone oxime under constant stirring, adding to this mixture a co-surfactant, if required, maintaining the solution at a temperature in the range of 15° C. to 40° C. for a period ranging from 10 minutes to 3 hours, neutralizing the excess acid with an aqueous solution of an alkali, filtering, extracting the filtrate with the solvent, and recycling the residue containing the unreacted cyclohexanone oxime and the surfactant back in to the process.

2. A process as claimed in claim 1, wherein the concentration of sulfuric acid is in the range of 0.1 moles/lit to 2.5 moles/lit.

3. A process as claimed in claim 1, wherein the anionic surfactant may be selected from sodium dodecyl sulfate, sodium dodecyl benzene sulfonate, sodium salt of dioctyl sulfosuccinate and the like.

4. A process as claimed in claim 1, wherein the concentration of the surfactants is in the range of 2 gm/lit to 40 gm/lit.

5. A process as claimed in claim 1, wherein the concentration of cyclohexanone oxime may range from 40 gm/lit to 100 gm/lit.

6. A process as claimed in claim 1, wherein co-surfactants such as medium chain alcohol, medium chain amine, and the like is also added if so necessary to the reaction mixture.

7. A process as claimed in claim 1, wherein the concentration of co-surfactant is in the range of 2 ml/lit to 50 ml/lit.

8. A process as claimed in claim 1, wherein the reaction mixture is neutralized by aqueous solution of an alkali selected from aqueous solution of ammonia, sodium hydroxide, potassium hydroxide and the like.

9. A process as claimed in claim 1, wherein the reaction mixture is filtered by known methods and the filtrate is extracted with organic solvents selected from benzene, toluene, diethylether, carbon tetrachloride and the like in the concentration range of 50 gm/lit to 600 gm/lit.

10. A process as claimed in claim 1, wherein the caprolactam formed, the unreacted cyclohexanone oxime and cyclohexanone formed are recovered from the filtrate by known methods.

* * * * *